(12) United States Patent
Valdez et al.

(10) Patent No.: US 9,901,444 B2
(45) Date of Patent: Feb. 27, 2018

(54) INVERTED VALVE STRUCTURE

(71) Applicant: Edwards Lifesciences Corporation, Irvine, CA (US)

(72) Inventors: Michael G. Valdez, Riverside, CA (US); Tram Ngoc Nguyen, Santa Ana, CA (US)

( * ) Notice: Subject to any disclaimer, the term of this patent is extended or adjusted under 35 U.S.C. 154(b) by 26 days.

(21) Appl. No.: 14/571,029

(22) Filed: Dec. 15, 2014

(65) Prior Publication Data
US 2015/0164636 A1   Jun. 18, 2015

Related U.S. Application Data

(60) Provisional application No. 61/917,032, filed on Dec. 17, 2013.

(51) Int. Cl.
  *A61F 2/06*  (2013.01)
  *A61F 2/24*  (2006.01)

(52) U.S. Cl.
  CPC .................................. *A61F 2/2412* (2013.01)

(58) Field of Classification Search
  CPC ........ A61F 2/24; A61F 2/2412; A61F 2/2475; A61F 2/2418
  USPC ....................................................... 623/1.27
  See application file for complete search history.

(56) References Cited

U.S. PATENT DOCUMENTS

| | | | |
|---|---|---|---|
| 2,292,003 A * | 8/1942 | Yant ...................... | F16K 15/148 137/512.15 |
| 3,312,237 A * | 4/1967 | Mon ..................... | A61F 2/2403 137/512.15 |
| 3,755,823 A | 9/1973 | Hancock | |
| 4,035,849 A | 7/1977 | Angell et al. | |
| 4,339,831 A * | 7/1982 | Johnson ................ | A61F 2/2418 137/512.15 |
| 4,510,628 A | 4/1985 | Kolff | |

(Continued)

FOREIGN PATENT DOCUMENTS

CN   202105047 U   1/2012
DE   19532846 A1   3/1997
(Continued)

OTHER PUBLICATIONS

Al-Khaja, et al. "Eleven Years' Experience with Carpentier-Edwards Biological Valves in Relation to Survival and Complications," European Journal of Cardiothoracic Surgery, vol. 3. pp. 305-311. 1989.

(Continued)

*Primary Examiner* — Brian Dukert
(74) *Attorney, Agent, or Firm* — Klarquist Sparkman, LLP; Joel B. German (57) ABSTRACT

Prosthetic valve embodiments are described herein that include a frame and a valve member mounted within the frame. The valve members can have a plurality of leaflets that are affixed to one another along their inflow edges, with articulating edges projecting from the inflow edges in the outflow direction. In an open configuration, the articulating edges can be collapsed radially inward by the forward flow of blood through the prosthetic valve, thereby creating a plurality of discrete flow areas between the frame and the inflow edges of the leaflets. In a closed configuration, the leaflets can be pushed radially outward by the reverse flow of blood, thereby closing the plurality of discrete flow areas.

19 Claims, 4 Drawing Sheets

(56) References Cited

U.S. PATENT DOCUMENTS

| | | | |
|---|---|---|---|
| 4,561,129 A * | 12/1985 | Arpesella | A61F 2/2412 623/2.17 |
| 4,731,075 A * | 3/1988 | Gallo Mezo | A61F 2/2403 623/2.17 |
| 4,777,951 A | 10/1988 | Cribier et al. | |
| 4,787,899 A | 11/1988 | Lazarus | |
| 4,796,629 A | 1/1989 | Grayzel | |
| 4,856,516 A | 8/1989 | Hillstead | |
| 4,878,495 A | 11/1989 | Grayzel | |
| 4,892,540 A * | 1/1990 | Vallana | A61F 2/2403 137/512.1 |
| 4,966,604 A | 10/1990 | Reiss | |
| 4,994,077 A | 2/1991 | Dobben | |
| 5,059,177 A | 10/1991 | Towne et al. | |
| 5,192,297 A | 3/1993 | Hull | |
| 5,282,847 A | 2/1994 | Trescony et al. | |
| 5,370,685 A | 12/1994 | Stevens | |
| 5,411,552 A | 5/1995 | Andersen et al. | |
| 5,449,384 A * | 9/1995 | Johnson | A61F 2/2418 623/2.14 |
| 5,545,214 A | 8/1996 | Stevens | |
| 5,554,185 A | 9/1996 | Block et al. | |
| 5,558,644 A | 9/1996 | Boyd et al. | |
| 5,584,803 A | 12/1996 | Stevens et al. | |
| 5,591,195 A | 1/1997 | Taheri et al. | |
| 5,607,464 A | 3/1997 | Trescony et al. | |
| 5,665,115 A | 9/1997 | Cragg | |
| 5,769,812 A | 6/1998 | Stevens et al. | |
| 5,800,508 A | 9/1998 | Goicoechea et al. | |
| 5,840,081 A | 11/1998 | Andersen et al. | |
| 5,855,597 A | 1/1999 | Jayaraman | |
| 5,925,063 A | 7/1999 | Khosravi | |
| 6,027,525 A | 2/2000 | Suh et al. | |
| 6,168,614 B1 | 1/2001 | Andersen et al. | |
| 6,221,091 B1 | 4/2001 | Khosravi | |
| 6,245,102 B1 | 6/2001 | Jayaraman | |
| 6,302,906 B1 | 10/2001 | Goecoechea et al. | |
| 6,425,916 B1 | 7/2002 | Garrison et al. | |
| 6,454,799 B1 | 9/2002 | Schreck | |
| 6,458,153 B1 | 10/2002 | Bailey et al. | |
| 6,461,382 B1 | 10/2002 | Cao | |
| 6,482,228 B1 | 11/2002 | Norred | |
| 6,527,979 B2 | 3/2003 | Constantz | |
| 6,582,462 B1 | 6/2003 | Andersen et al. | |
| 6,652,578 B2 | 11/2003 | Bailey et al. | |
| 6,730,118 B2 | 5/2004 | Spenser et al. | |
| 6,733,525 B2 | 5/2004 | Yang et al. | |
| 6,767,362 B2 | 7/2004 | Schreck | |
| 6,830,584 B1 | 12/2004 | Seguin | |
| 6,878,162 B2 | 4/2005 | Bales et al. | |
| 6,893,460 B2 | 5/2005 | Spenser et al. | |
| 6,908,481 B2 | 6/2005 | Cribier | |
| 7,018,406 B2 | 3/2006 | Seguin et al. | |
| 7,018,408 B2 | 3/2006 | Bailey et al. | |
| 7,175,656 B2 * | 2/2007 | Khairkhahan | A61F 2/2403 606/200 |
| 7,276,078 B2 | 10/2007 | Spenser et al. | |
| 7,276,084 B2 | 10/2007 | Yang et al. | |
| 7,318,278 B2 | 1/2008 | Zhang et al. | |
| 7,374,571 B2 | 5/2008 | Pease et al. | |
| 7,393,360 B2 | 7/2008 | Spenser et al. | |
| 7,462,191 B2 | 12/2008 | Spenser et al. | |
| 7,510,575 B2 | 3/2009 | Spenser et al. | |
| 7,585,321 B2 | 9/2009 | Cribier | |
| 7,618,446 B2 | 11/2009 | Andersen et al. | |
| 7,655,034 B2 | 2/2010 | Mitchell et al. | |
| 7,785,366 B2 | 8/2010 | Maurer et al. | |
| 7,959,672 B2 | 6/2011 | Salahieh et al. | |
| 7,993,394 B2 | 8/2011 | Hariton et al. | |
| 8,029,556 B2 | 10/2011 | Rowe | |
| 8,167,932 B2 | 5/2012 | Bourang | |
| 8,246,675 B2 * | 8/2012 | Zegdi | A61F 2/2418 623/1.24 |
| 8,449,606 B2 | 5/2013 | Eliasen et al. | |
| 8,506,620 B2 * | 8/2013 | Ryan | A61F 2/2418 623/1.24 |
| 2002/0026094 A1 | 2/2002 | Roth | |
| 2002/0032481 A1 | 3/2002 | Gabbay | |
| 2002/0138135 A1 | 9/2002 | Duerig et al. | |
| 2003/0050694 A1 | 3/2003 | Yang et al. | |
| 2003/0055492 A1* | 3/2003 | Shaolian | A61F 2/2418 623/1.24 |
| 2003/0100939 A1 | 5/2003 | Yodfat et al. | |
| 2003/0158597 A1 | 8/2003 | Quiachon | |
| 2003/0212454 A1 | 11/2003 | Scott et al. | |
| 2004/0039436 A1 | 2/2004 | Spenser et al. | |
| 2004/0186563 A1 | 9/2004 | Lobbi | |
| 2004/0186565 A1 | 9/2004 | Schreck | |
| 2004/0260389 A1 | 12/2004 | Case et al. | |
| 2005/0096736 A1 | 5/2005 | Osse et al. | |
| 2005/0203614 A1 | 9/2005 | Forster et al. | |
| 2005/0203617 A1 | 9/2005 | Forster et al. | |
| 2005/0234546 A1 | 10/2005 | Nugent et al. | |
| 2006/0025857 A1 | 2/2006 | Bergheim et al. | |
| 2006/0058872 A1 | 3/2006 | Salahieh et al. | |
| 2006/0149350 A1 | 7/2006 | Patel | |
| 2007/0005131 A1 | 1/2007 | Taylor | |
| 2007/0010877 A1 | 1/2007 | Salahieh et al. | |
| 2007/0093887 A1* | 4/2007 | Case | A61F 2/2418 623/1.24 |
| 2007/0112422 A1 | 5/2007 | Dehdashtian | |
| 2007/0203503 A1 | 8/2007 | Salahieh et al. | |
| 2007/0203575 A1 | 8/2007 | Forster et al. | |
| 2007/0265700 A1 | 11/2007 | Eliasen et al. | |
| 2008/0114442 A1 | 5/2008 | Mitchell et al. | |
| 2008/0125853 A1 | 5/2008 | Bailey et al. | |
| 2009/0157175 A1 | 6/2009 | Benichou | |
| 2009/0276040 A1 | 11/2009 | Rowe et al. | |
| 2009/0281619 A1 | 11/2009 | Le et al. | |
| 2009/0306768 A1* | 12/2009 | Quadri | A61F 2/2418 623/1.26 |
| 2009/0319037 A1 | 12/2009 | Rowe et al. | |
| 2010/0049313 A1 | 2/2010 | Alon et al. | |
| 2010/0198347 A1 | 8/2010 | Zakay et al. | |
| 2011/0015729 A1 | 1/2011 | Jimenez et al. | |
| 2012/0123529 A1 | 5/2012 | Levi et al. | |
| 2013/0018456 A1 | 1/2013 | Li et al. | |
| 2013/0023985 A1 | 1/2013 | Khairkhahan et al. | |
| 2013/0150956 A1 | 6/2013 | Yohanan et al. | |
| 2013/0317598 A1 | 11/2013 | Rowe et al. | |
| 2016/0235529 A1* | 8/2016 | Ma | A61F 2/2418 |

FOREIGN PATENT DOCUMENTS

| | | |
|---|---|---|
| DE | 19546692 A1 | 6/1997 |
| DE | 19857887 A1 | 7/2000 |
| DE | 19907646 A1 | 8/2000 |
| EP | 0103546 A1 | 3/1984 |
| EP | 0592410 A1 | 10/1995 |
| EP | 0850607 A1 | 7/1998 |
| EP | 0597967 A1 | 12/1999 |
| EP | 1796597 A2 | 6/2007 |
| FR | 2788217 A1 | 7/2000 |
| FR | 2815844 | 5/2002 |
| SU | 1271508 A1 | 11/1986 |
| WO | 1991017720 A1 | 11/1991 |
| WO | 1993001768 A1 | 2/1993 |
| WO | 1998029057 A1 | 7/1998 |
| WO | 1999040964 A1 | 8/1999 |
| WO | 1999047075 A1 | 9/1999 |
| WO | 2005034812 A1 | 4/2005 |
| WO | 2005084595 A1 | 9/2005 |
| WO | 2005102015 A2 | 11/2005 |
| WO | 2006111391 A1 | 10/2006 |
| WO | 2006/138173 A2 | 12/2006 |
| WO | 2007047488 A2 | 4/2007 |
| WO | 2007067942 A1 | 6/2007 |
| WO | 2007097983 A2 | 8/2007 |
| WO | 2008/005405 A2 | 1/2008 |
| WO | 2008091515 A2 | 7/2008 |

(56) References Cited

FOREIGN PATENT DOCUMENTS

| WO | 2009033469 A1 | 3/2009 |
|---|---|---|
| WO | 2010121076 A2 | 10/2010 |
| WO | 2013086413 A1 | 6/2013 |

OTHER PUBLICATIONS

Bailey, S. "Percutaneous Expandable Prosthetic Valves," Textbook of Interventional Cardiology vol. 2, 2nd Ed. pp. 1268-1276. 1994.
H.R. Andersen "History of Percutaneous Aortic Valve Prosthesis," Herz No. 34. pp. 343-346. 2009.
H.R. Andersen, et al. "Transluminal Implantation of Artificial Heart Valve. Description of a New Expandable Aortic Valve and Initial Results with implantation by Catheter Technique in Closed Chest Pig," European Heart Journal, No. 13. pp. 704-708. 1992.
Pavcnik, et al. "Development and initial Experimental Evaluation of a Prosthetic Aortic Valve for Transcatheter Placement," Cardiovascular Radiology, vol. 183, No. 1. pp. 151-154. 1992.
Ross, "Aortic Valve Surgery," at a meeting of the Council on Aug. 4, 1966. pp. 192-197.
Sabbah, et al. "Mechanical Factors in the Degeneration of Porcine Bioprosthetic Valves: An Overview," Journal of Cardiac Surgery, vol. 4, No. 4. pp. 302-309. 1989.
Uchida, "Modifications of Gianturco Expandable Wire Stents," American Journal of Roentgenology, vol. 150. pp. 1185-1187. 1986.
Wheatley, "Valve Prostheses," Operative Surgery, 4th ed. pp. 415-424. 1986.

* cited by examiner

INVERTED VALVE STRUCTURE

CROSS-REFERENCE TO RELATED APPLICATION

The present application claims the benefit of U.S. Provisional Application No. 61/917,032, filed Dec. 17, 2013, which is incorporated herein by reference.

FIELD

This disclosure relates generally to prosthetic valves and methods for introducing the prosthetic valves into the body.

BACKGROUND

Prosthetic valves have been used for many years to treat valvular disorders. Native valves, including heart valves (such as the aortic, pulmonary, tricuspid, and mitral valves), serve critical functions in assuring the forward flow of an adequate supply of blood through the cardiovascular system. These valves can be rendered less effective by congenital, inflammatory, or infectious conditions. Such damage to the valves can result in serious cardiovascular compromise or death. For many years the definitive treatment for such disorders was the surgical repair or replacement of the valve during open heart surgery, but such surgeries are prone to many complications.

Transvascular techniques have also been developed for introducing and implanting a prosthetic valve using a flexible catheter in a manner that is less invasive than open-heart surgery. For example, a prosthetic valve can be mounted in a crimped state on the end-portion of a flexible catheter and advanced through a blood vessel of the patient until the prosthetic valve reaches the implantation site. The prosthetic valve at the catheter tip can then be expanded to its functional size at the site of the defective native valve such as by inflating a balloon on which the prosthetic valve is mounted. Alternatively, the prosthetic valve can have a resilient, self-expanding stent or frame that self-expands the prosthetic valve to its functional size when advanced from a delivery sheath at the distal end of the catheter.

Prosthetic valves generally consist of a cylindrical stent-like frame and leaflets. The leaflets typically have fixed, inflow edges that are sutured continuously along an interior circumference of the cylindrical frame. Blood flows through the prosthetic valve when all the leaflets open and lie against the inner surface of the prosthetic valve frame, creating a single, circular channel. Conversely, the prosthetic valve closes when the leaflets are deflected inwardly and coapt against each other, similarly to a native heart valve. Unfortunately, prosthetic valves can suffer from paravalvular leaks (PVL), or blood leaking around the outside of the prosthetic valve. A need therefore exists for a stented bioprosthetic valve which minimizes PVL and/or other sources of regurgitation through the prosthetic valve.

SUMMARY

Embodiments of prosthetic valves are described herein that include a stent/frame and a valve member mounted within the frame. The valve members can comprise a plurality of leaflets, each with an articulating edge and an inflow edge that extends across the stent/frame lumen between commissure tabs spaced angularly apart along an interior circumference of the frame. Adjacent leaflets can be affixed to one another along these inflow edges, with articulating edges projecting from the inflow edges in the outflow direction with the forward flow of blood. In an open configuration, the leaflets can be collapsed radially inward by the forward flow of blood through the prosthetic valve, thereby creating a plurality of discrete flow areas between the frame and the inflow edges of the leaflets. In a closed configuration, the articulating edges of the leaflets can be pushed radially outward by the reverse flow of blood, thereby closing the plurality of discrete flow areas.

In one aspect, a prosthetic valve is provided having a valve member and an annular frame with an inflow end, an outflow end, and a longitudinal axis extending from the inflow end to the outflow end. The valve member can be mounted within the annular frame and can comprise a plurality of flexible leaflets. The valve member can be located between the inflow end and the outflow end of the annular frame. Each leaflet can comprise an inflow surface, an outflow surface, a substantially non-articulating inflow edge, and at least one articulating outflow edge. Adjacent leaflets can be affixed to one another along their respective inflow edges. In an open configuration, the leaflets can be collapsed radially inward by the forward flow of blood through the prosthetic valve, thereby creating a plurality of discrete flow areas between the frame and the inflow edges of the leaflets. In a closed configuration, the leaflets can be pushed radially outward by the reverse flow of blood, thereby closing the plurality of discrete flow areas.

In some embodiments, each of the inflow edges extend between two points spaced circumferentially apart an interior circumference of the frame. The inflow edges of the adjacent leaflets can be joined together directly without the aid of a mechanical support member extending between the points.

In some embodiments, a pocket is formed between the leaflets, in the open configuration, which faces the outflow end and is bordered by the articulating edges and the outflow surfaces of the leaflets. In some embodiments, the pocket can be configured such that reverse flow entering into the pocket forces the leaflets radially outward.

In some embodiments, in the open configuration, the inflow edges and the leaflets together form a three-pointed star arrangement.

In some embodiments, in the closed configuration, the articulating edges are in contact with the frame and/or a skirt lining an interior surface of the frame.

In some embodiments, in the closed configuration, the outflow surfaces face the outflow end of the prosthetic valve, and the inflow surfaces face the inflow end of the prosthetic valve.

In some embodiments, the annular frame is a collapsible and expandable annular frame that is configured to be collapsed to a radially collapsed state for mounting on a delivery apparatus and expanded to a radially expanded state inside the body.

In some embodiments, the inflow edges of the leaflets have outer edge portions adjacent the frame, and the inflow edges define a central hub, which is at substantially the same longitudinal position relative to a longitudinal axis of the prosthetic valve as the outer edge portions.

In another aspect, a method of transmitting blood through a prosthetic valve is provided, comprising providing a prosthetic valve having a frame and a plurality of leaflets located between an inflow end and an outflow end of the frame. Each leaflet can have an inflow surface, an outflow surface, an inflow edge and at least one articulating outflow edge. The method further comprises collapsing the plurality of leaflets in a radially inward direction to permit the forward flow of blood through the prosthetic valve; and expanding the leaflets radially outward towards an interior surface of the frame to substantially prevent the reverse flow of blood through the prosthetic valve.

In some embodiments, a pocket is formed between the collapsed leaflets, wherein the pocket faces the outflow end.

In some embodiments, the expanding comprises causing the inflow surfaces to face the inflow end and causing the outflow surfaces to face the outflow end.

In some embodiments, the expanding comprises causing at least one of the articulating edges of each leaflet to contact the frame and/or a skirt lining an interior of the frame.

In some embodiments, the expanding comprises allowing reverse blood flow to enter into the pocket and force the leaflets radially outward.

In some embodiments, the collapsing creates multiple discrete flow areas between the leaflets and inside of the frame.

In another aspect, a method of implanting a prosthetic valve is provided, comprising implanting into a patient's body a prosthetic valve having a frame and a plurality of leaflets located between an inflow end and an outflow end of the frame. A pressure gradient in a first direction can cause the plurality of leaflets of the prosthetic valve to collapse radially inwardly to permit the forward flow of blood through the prosthetic valve, and a pressure gradient in a second direction can cause the plurality of leaflets to expand radially outward to substantially prevent the reverse flow of blood through the prosthetic valve.

In some embodiments, the pressure gradient in the second direction causes inflow surfaces of the leaflets to face an inflow end of the prosthetic valve and outflow surfaces of the leaflets to face an outflow end of the prosthetic valve.

In some embodiments, the pressure gradient in the second direction causes at least one articulating edge of each leaflet to contact a frame of the prosthetic valve and/or a skirt lining an interior of the frame.

In some embodiments, the expanding of the plurality of the leaflets comprises expanding a pocket formed between the leaflets, the pocket facing the outflow end of the prosthetic valve.

In some embodiments, the radial collapsing of the plurality of leaflets creates multiple discrete flow areas between the leaflets.

The foregoing and other objects, features, and advantages of the disclosed technology will become more apparent from the following detailed description, which proceeds with reference to the accompanying figures.

DETAILED DESCRIPTION

Prosthetic valve embodiments are disclosed herein having a stent/frame defining a lumen and plurality of leaflets that can flex inwardly to open and flex outwardly to close. Rather than having contoured inflow edges that are sutured circumferentially to the frame, the leaflets can each have inflow edges that extend out across the lumen, between commissure tabs spaced circumferentially apart along an interior circumference of the frame. Each inflow edge can be sutured (or otherwise attached) along its length to the inflow edge(s) of adjacent leaflet(s). Discrete flow areas can thus be created between each leaflet inflow edge and the interior stent wall. Articulating edges of the leaflets can project from their respective inflow edges in the outflow direction, with forward blood flow. The leaflets can thus move, between an open position and a closed position, in response to differences in fluid pressure between the inflow and outflow ends of the prosthetic valve.

When blood flows through the prosthetic valve from the inflow end in the outflow direction, the leaflets can be pushed radially inward against one another towards the center of the lumen, thereby defining discrete flow passages between the frame and the inflow edges of the leaflets. Reverse blood flow (from the outflow end in the inflow direction) can enter into a space between the leaflets (towards the center of the lumen) that faces the outflow end, pushing the articulating edges of the leaflets radially outward to close the prosthetic valve. In this closed configuration, the leaflets can effectively seal off various potential leak paths to reverse flow, such as space(s) located between the leaflets and the skirt and/or any spaces between the leaflets themselves.

While additional structural elements can optionally be included to coordinate or otherwise assist in the radial movements of the leaflets, such additional elements are not necessary in the disclosed embodiments. Thus, in various embodiments, the leaflets can expand radially outward to assume a closed configuration, and collapse inward to assume an open configuration, without the aid of mechanical arms, springs, struts, or other appendages. In particular, the inflow edges of the adjacent leaflets can be joined together directly without the aid of a mechanical support member (such as an arm, strut, spring, or other appendage) extending between them (e.g., between two points spaced circumferentially apart along an interior circumference of the frame).

The prosthetic valve 10 is adapted to be deployed in the native aortic annulus, although it also can be adapted to replace other native valves of the heart (the mitral, pulmonary, and/or tricuspid valve). Moreover, the prosthetic valve 10 can be adapted to replace other valves within the body, such as venous valves.

Figure 1:
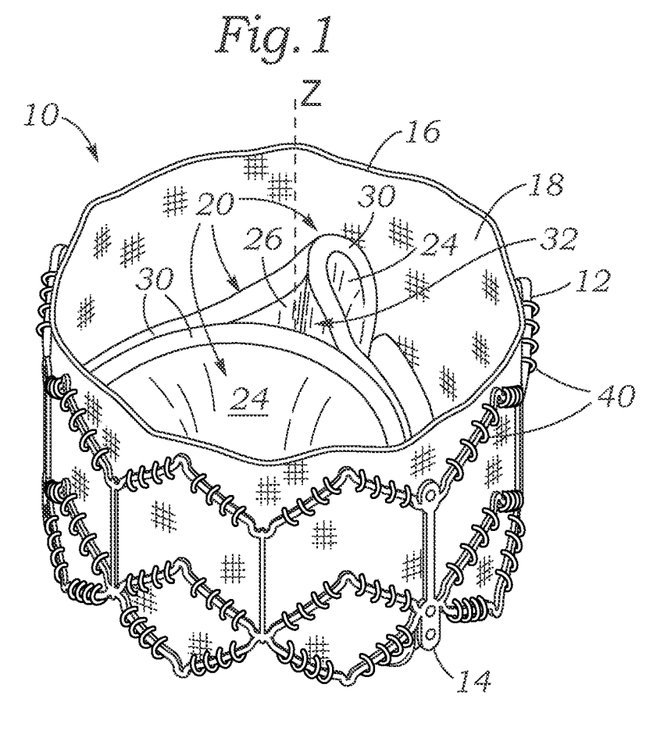
FIG. 1 is a perspective view of a prosthetic valve embodiment, in an open configuration.
Figure 2:
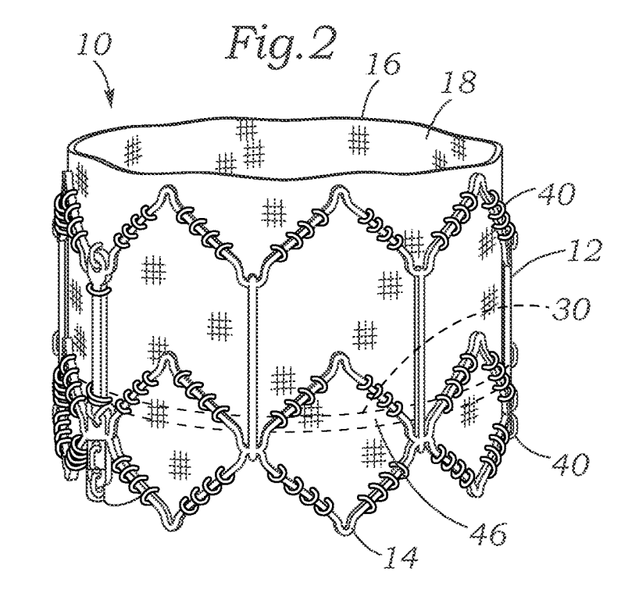
FIG. 2 is a side view of the prosthetic valve embodiment of FIG. 1, in a closed configuration.

Referring now to FIGS. 1-2, a prosthetic valve 10, according to one embodiment, can comprise an annular frame or stent 12 having an inflow end 14 and an outflow end 16 defining a longitudinal axis Z (FIG. 1), and a skirt 18 mounted to the frame 12. The skirt 18 can be an annular skirt positioned inside of the frame 12 as shown. The skirt 18 can comprise a fabric, tissue, membrane, or other material, and can insulate the leaflets 20 from dilapidation or damage that may result from direct contact with the frame 12. If desired, an outer skirt (not shown) can be secured around the outside of the frame 12, for example, to facilitate sealing of the frame 12 against the native annulus and/or reduce damage to the native annulus. Some embodiments of an inner skirt and outer skirt are unitary, while other embodiments use two or more pieces of material.

Between the inflow and outflow ends 14, 16 of the prosthetic valve is a valve member comprising a plurality of flexible leaflets 20. As shown in FIGS. 3-5 and 7, each leaflet 20 can comprise two commissure tabs 22, spaced angularly apart along an interior circumference of the frame 12. The skirt 18 can be secured to the frame 12, such as with sutures 40. Each commissure tab 22 can be rolled up and connected to a commissure tab of an adjacent leaflet, such as by sutures, so as to define respective commissures of the leaflets 20. The commissure tabs 22 can also be sutured to the frame 12 and/or the skirt 18. As shown in the figures, the prosthetic valve 10 can have a set of three leaflets 20 in a tricuspid arrangement. In other embodiments, the prosthetic valve 10 can have a different number of leaflets, such as two leaflets (e.g., a bicuspid arrangement) or four leaflets.

Figure 3:
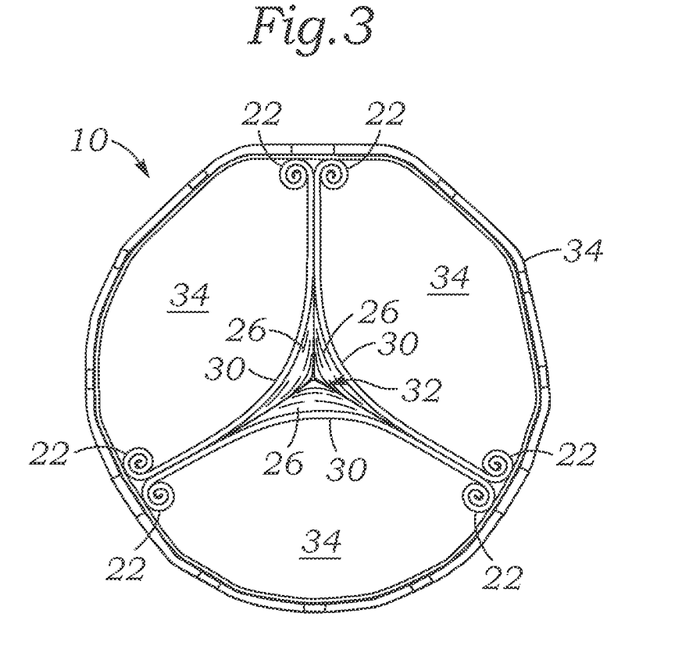
FIG. 3 is an outflow view of the prosthetic valve embodiment of FIG. 1, in an open configuration.
Figure 4:
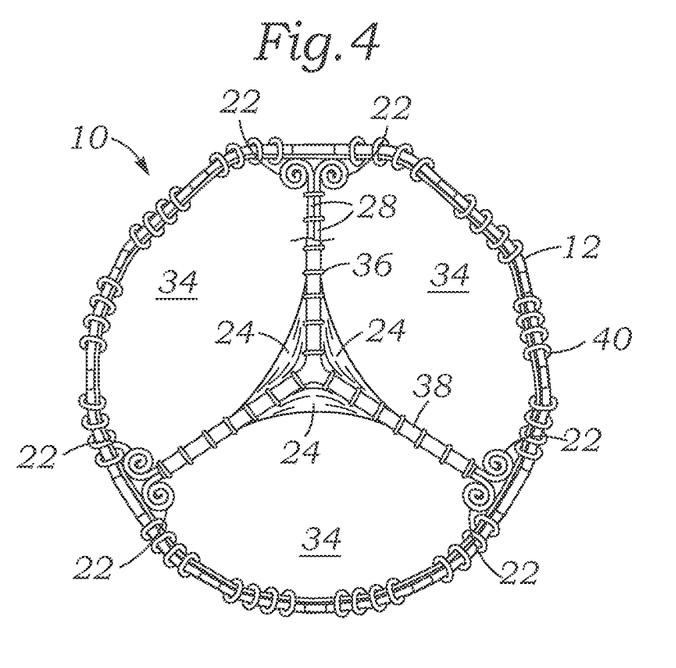
FIG. 4 is an inflow view of the prosthetic valve embodiment of FIG. 1, in an open configuration.
Figure 5:
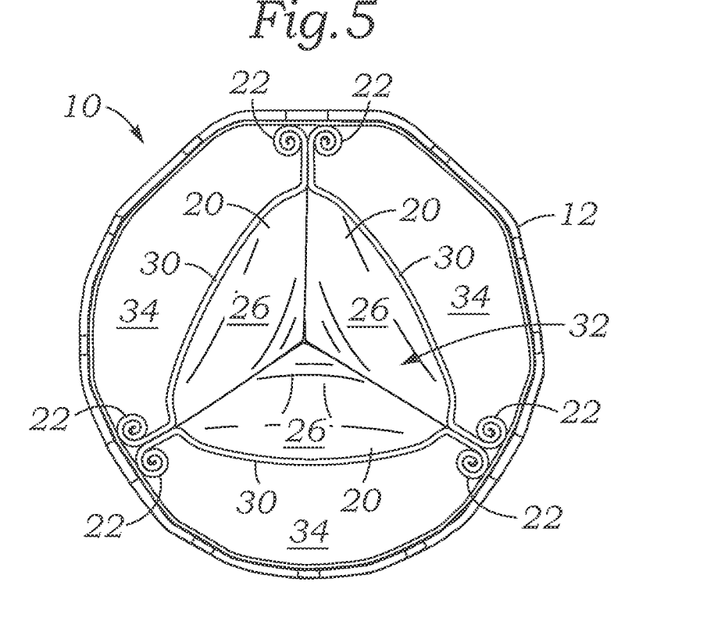
FIG. 5 is an outflow view of the prosthetic valve embodiment of FIG. 1, in a partially closed configuration.
Figure 7:
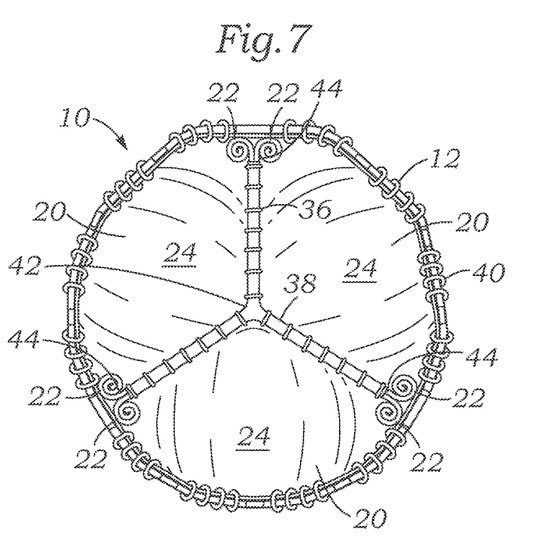
FIG. 7 is an inflow view of the prosthetic valve embodiment of FIG. 1, in a closed configuration.

The leaflets 20 can each further comprise an inflow surface 24, an outflow surface 26, an inflow edge 28 (FIGS. 4 and 7) extending between the commissure tabs 22, and at least one articulating edge 30 (FIGS. 1, 3 and 5). The articulating edges 30 can be configured to project from the inflow edges 28 in the direction of the outflow end 16 with the forward flow of blood. As shown in FIGS. 4 and 7, adjacent leaflets 20 can be securely attached to each other in the vicinity of the respective inflow edges 28, such as by transverse sutures 36 (orthogonal to the inflow edges 28) and/or any other biocompatible adhesive known to those of skill in the art. The transverse sutures 36 may optionally be accompanied by longitudinal sutures (in the direction of the inflow edges 28) (not shown). Thus, in various embodiments, the inflow edges 28 are substantially non-articulating. As shown in FIGS. 4 and 7, the inflow edge 28 of each leaflet can be affixed to the inflow edges of the other two leaflets. In particular, adjacent inflow edges 28 can be covered by a reinforcing layer 38 to help secure the leaflets 20 together, with sutures passing through the inflow edges 28 and the reinforcing layer 38. The reinforcing layer 38 can be, for example, a fabric (e.g., woven polyethylene terephthalate (PET), DACRON®), a tissue layer, or any of the various other materials that are used to form skirt 18, as further described below.

The inflow edges 28 can each follow an angled course from the frame 12 to the center of the prosthetic valve and back to the frame 12. As shown (for a prosthetic valve 10 having three leaflets 20), the angle defined by each leaflet 20 at the center of the prosthetic valve 10 can be about 120°, and the total of all of these angles can be about 360°. In other embodiments, the angled courses of the inflow edges differ from one another, but still add up to 360°. In some embodiments, there are greater or fewer than three leaflets, and the angled course varies accordingly. For example, a prosthetic valve may have four leaflets in a quadricuspid arrangement, with inflow edges each following an angled course of about 90°.

Figure 8:
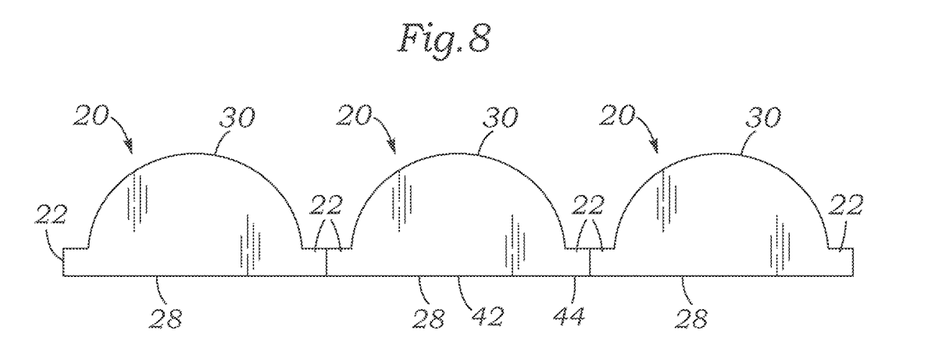
FIG. 8 is a side elevation view of a leaflet assembly can be used in the prosthetic valve embodiment of FIG. 1, shown in an unrolled or flattened configuration.

In the illustrated embodiment, the inflow edges 28 together define a plane that is generally perpendicular to the axis Z. As best seen in FIGS. 7 and 8, a hub 42 of the inflow edges 28 of the leaflets is at substantially the same longitudinal position as the edge portions 44 thereof. In other embodiments (not illustrated), the hub 42 is longitudinally offset, for example, towards the inflow end 14 or outflow end 16 relative to the edge portions 44 of the inflow edges. Some embodiments in which the hub 42 is longitudinally offset exhibit improved radial compressibility compared to similar prosthetic valves 10 in which the central hub 42 is not longitudinally offset, for example, because the suture 36 and/or reinforcing fabric 38 are distributed over a greater longitudinal distance, resulting in less bunching. In some embodiments, at least one edge portion 44 is displaced longitudinally.

In some embodiments in which the hub 42 is offset towards the inflow end 14, the central hub 42 extends farther upstream than any portion of the frame 12. In other embodiments, the hub 42 and the most upstream portion of the frame 12 have substantially the same longitudinal position. In other embodiments, the hub 42 is disposed downstream of the most upstream portion of the frame 12. As discussed in greater detail below, some embodiments of the inflow edges 28 are equipped with additional support members. In some embodiments, one or more portions of the inflow edge 28, for example, the hub 42 is suspended from the frame 12 in the radially expanded configuration, for example, using suture, thread, fibers, or wire.

Some embodiments of the hub 42 are offset radially from the center of the frame 12, for example, where the frame is non-circular, for example, oval or D-shaped, and/or where an offset flow axis is desired. The radial offset is combinable with a longitudinal offset of the hub 42 and/or edge portion(s) discussed above.

As best shown in FIGS. 1 and 3, the articulating edges 30 may each follow a contoured course, with an apex approximately half-way between the commissure tabs 22 of each of the leaflets 20. Alternatively, the apex of an articulating edge 30 can be located closer to one of the two commissure tabs 22 than the other.

In various embodiments, instead of having a single curved articulating edge 30, one or more of the leaflets 20 can multiple articulating edges, depending upon the shape of the leaflets 20, such as two, three or four articulating edges. Thus, in some embodiments, the leaflets 20 can be polygonal-shaped, with a single inflow edge 28 and multiple articulating edges, such as two, three, four or five articulating edges. In some embodiments, the articulating edges 30 are free edges (i.e., no connected structures), whereas in other embodiments, the articulating edges 30 are connected to cord(s) or other structures. In some embodiments, one or more of the leaflets 20 has a combination of free and non-free articulating edges 30.

FIG. 1 shows the outflow end of the prosthetic valve 10 in an open configuration, with the articulating edges 30 located in a radially inward position and the outflow surfaces 26 facing each other. In this configuration, blood can flow through multiple discrete areas 34 (FIGS. 3-4) located between the frame 12 and the leaflets 20. As shown in FIGS. 3-4, the prosthetic valve in an open configuration can form a three-spoke-wheel or an encircled three-pointed star arrangement (i.e., similar to a Mercedes-Benz® logo), as viewed from either end 14, 16 of the prosthetic valve. Even though the leaflets 20 are collapsed by the forward blood flow into this radially inward collapsed position, a vestigial or reduced pocket 32 can remain between the leaflets 20, facing the outflow direction and bordered by the articulating edges 30 and the outflow surfaces 26. This pocket 32 can be configured to capture any reverse blood flow (i.e., flow towards the inflow direction) or back pressure that may occur subsequent to the passage of a pulse of forward blood flow. Blood flow or pressure thus entering into the pocket 32 can exert force on the outflow surfaces 26, thereby pushing each leaflet 20 radially outward, with the articulating edges 30 spread radially apart towards the frame 12 to close the prosthetic valve 10. In one embodiment, as shown in FIGS.

1 and 3, the pocket 32 can be substantially triangular-shaped. In various other embodiments, this pocket 32 can assume various other shapes, depending upon the number and orientation of leaflets in the prosthetic valve, such as a rectangular, square or other polygonal shape. In some embodiments, the inflow surfaces 24 can be concave in the open and/or the closed configurations. Likewise, in some embodiments, the outflow surfaces 26 can be convex in the open and/or the closed configurations.

Figure 6:
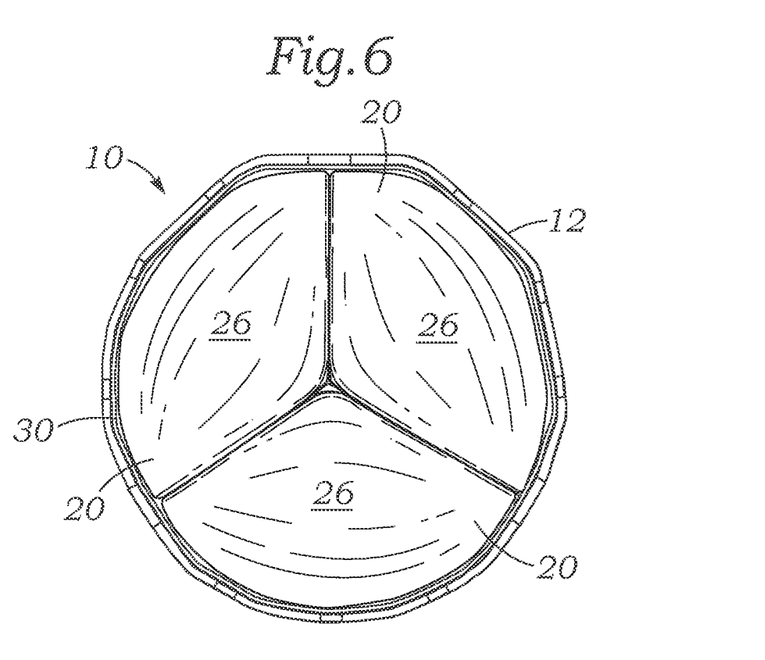
FIG. 6 is an outflow view of the prosthetic valve embodiment of FIG. 1, in a closed configuration.

FIGS. 6-7 show the prosthetic valve 10 in a closed configuration, with the leaflets 20 forced fully outward. In this configuration, the articulating edges 30 can be spread maximally apart, such that each articulating edge 30 is in contact with the frame 12 and/or the skirt 18. As shown, interiors of the leaflets 20 can be substantially co-planar, such that the interiors of the leaflets 20 generally lie in a plane that is substantially perpendicular to the longitudinal axis Z with some puckering or cupping of the leaflet. As such, the leaflets 20 can extend radially outwards to cover the outflow facing sides of the commissure tabs 22, as shown in FIG. 6. The articulating edges 30 can each extend to contact the skirt 18 and/or the frame 12, thus effecting closure of the prosthetic valve 10.

In the illustrated embodiment, the leaflets 20 are oversized such that the articulating edges 30 define an upturned rim 46 (FIG. 2) extending towards the outflow end 16, the rim 46 coapting with or sealing against the skirt 18, thereby preventing backflow of blood or fluid. The oversizing also allows the leaflets 20 to accommodate deployment in a non-circular native valve annulus, in which the frame 12 assumes a non-circular cross-sectional shape, in some embodiments. In this closed position, the outflow surfaces 26 can generally face the outflow end 16, and the inflow surfaces 24 can generally face the inflow end 14. Thus, in some embodiments, no discernible pocket may remain between the leaflets 20 in the closed configuration.

In some embodiments, the leaflets 20 at least partially overlap in the closed configuration, such that the inflow surface 24 of one leaflet can at least partially cover the outflow surface 26 of another leaflet. In other embodiments, the leaflets 20 do not significantly overlap in the closed configuration.

In some embodiments, all of the leaflets 20 are formed from a single sheet (or other single piece) of leaflet material. FIG. 8 shows an exemplary unitary sheet of leaflet material forming three leaflets 20 connected side-by-side in a flattened configuration. The leaflets 20 can have scalloped articulating edges 30 and straight inflow edges 28. In other embodiments, the inflow edges 28 and/or articulating edges 30 independently have another shape, for example, convex, concave, arcuate, and/or angled. In particular, the articulating edges 30 are suitably shaped in embodiments in which the hub 42 is radially offset and/or the frame 12 is non-circular. The opposite ends of the sheet can be secured together to form a tubular configuration. The sheet of leaflet material can then be folded to form the three leaflets 20, with the inflow edges 28 joined together as described herein such that the leaflets 20 can assume their operating configurations.

Alternatively, instead of folding a unitary sheet to form the leaflets, the sheet of leaflet material can be cut to form three separate leaflets 20, which can then be secured to each other in the matter described above and shown in the figures. In another embodiment, the leaflets 20 are each cut separately from a sheet of leaflet material, at adjacent and/or non-adjacent locations along the sheet of leaflet material.

The leaflets 20 can be formed of pericardial tissue (e.g., bovine pericardial tissue), biocompatible synthetic materials, or various other suitable natural or synthetic materials as known in the art and described in U.S. Pat. No. 6,730,118, which is incorporated by reference herein. In one embodiment, the leaflets 20 are sutured together, and a thin fabric (such as woven PET) or tissue material is wrapped (or otherwise placed) atop the sutured areas during manufacture to hold the leaflets 20 securely in place and/or to prevent cutting of the leaflet material. The tissue or fabric may be biocompatible, such that it can remain in this position when implanted.

In the illustrated embodiment, the inflow edges 28 are joined together without incorporating any additional supporting members or framework. In other words, the inflow edges 28 of the valve 10 are self-supporting. Other embodiments (not illustrated) include at least one or more additional supporting members at the inflow edges 28, for example, struts or beams. The additional supporting member(s) can be internal, for example, enclosed by the leaflets 20 and/or reinforcing layer 38, or external, for example, exposed. Some embodiments of the additional supporting member(s) are coupled directly to the frame 12, while other embodiments are coupled to the frame indirectly through the leaflets 20 and/or reinforcing layer 38. Some embodiments of the additional supporting member(s) independently comprise one or more materials discussed below as frame materials. In some embodiments, the additional support members include guy wires, thread, fiber, or suture extending between selected locations of the inflow edges, for example, the hub 42 and the frame 12, for example, the inflow end 14.

The skirt 18 can comprise a thin, flexible sheet of material, and can be made of any of various suitable materials, such as a fabric (e.g., polyethylene terephthalate (PET) (sold under the tradename DACRON®), ultra-high-molecular-weight polyethylene (UHMWPE) (sold under the tradename DYNEEMA PURITY®), etc.), tissue (e.g., pericardial tissue), PTFE, metal, sponge, or polymer. In the illustrated embodiment, the skirt 18 desirably extends the full length of the frame 12 from the inflow end 14 to the outflow end 16. In other embodiments, the skirt 18 can extend less than the full length of the frame 12, such as from the inflow end 14 to a location on the frame at about the same axial position of the articulating edges 30 of the leaflets in their open position.

The frame 12 can be a collapsible and expandable annular frame that is configured to be collapsed to a radially collapsed state for mounting on a delivery apparatus and expanded to a radially expanded state inside the body. The frame 12 can be configured such that, in the radially expanded state, no frame component or mechanical strut/arm or other appendage extends into lumen or extends radially inward toward the central longitudinal axis of the frame.

As used herein, the term "annular" can refer to a frame having any closed shape in cross-section (taken along a plane perpendicular to the longitudinal axis Z), including but not limited to a circular/ring shape, or a square/rectangular shape, a polygonal shape, a trefoil, or elliptical shape. Likewise, an annular frame can have various three-dimensional structures, including but not limited to a cylindrical structure (as shown in the figures) or a non-cylindrical tubular structure having a cross-sectional profile (taken along a plane perpendicular to the longitudinal axis Z) that varies along its length. As shown in FIGS. 1 and 2, the frame 12 can comprise a plurality of circumferential rows of zig-zag struts, connected by longitudinal struts. U.S. Pat.

No. 7,993,394, hereby incorporated by reference in its entirety, provides additional description of various frame embodiments that can be used in the prosthetic valve embodiments disclosed herein. The frame 12 can also be non-collapsible and/or non-expandable, such as for surgical implantation.

In certain embodiments, the frame 12 can be made of any of various suitable plastically-expandable materials or self-expanding materials (e.g., a nickel-titanium alloy, such as Nitinol) as known in the art. Suitable plastically-expandable materials that can be used to form the frame 12 include, without limitation, stainless steel, a nickel-based alloy (e.g., a nickel-cobalt-chromium alloy), polymers, or combinations thereof. In particular embodiments, frame 12 is made of a nickel-cobalt-chromium-molybdenum alloy, such as UNS R30035 (covered by ASTM F562-02), commercially available as MP35N® (SPS Technologies), which comprises 35% nickel, 35% cobalt, 20% chromium, and 10% molybdenum, by weight. When the frame 12 is constructed of a plastically-expandable material, the prosthetic valve 10 can be crimped to a radially compressed state on a balloon (or other expansion device) of a delivery apparatus.

The prosthetic valve embodiments disclosed herein can be surgically implanted and/or can be delivered using a delivery apparatus, such as a catheter. The delivery apparatus can be inserted into the patient's vasculature and advanced through the patient's body using known techniques. In one implementation, the prosthetic valve is delivered in a trans-femoral procedure in which the delivery apparatus is inserted into a femoral artery and advanced through the aorta to the native aortic valve (or another native valve of the heart). In another implementation, the prosthetic valve can be delivered in a transventricular procedure in which the delivery apparatus is inserted through a small surgical opening in the chest and another surgical opening in the wall of the left ventricle of the heart, such as an opening made at the bare spot on the lower anterior ventricle wall. In another implementation, the prosthetic valve can be delivered in a transaortic procedure in which the delivery apparatus is inserted through a small surgical opening in the chest and another surgical opening in the ascending aorta, at a location above the aortic valve. In another implementation, the prosthetic valve is a replacement venous valve for implantation in a vein, or a replacement for another valve with a lower flow rate relative to the aortic valve.

When the prosthetic valve is positioned at the desired deployment location (e.g., within the native aortic valve), the balloon of the delivery apparatus can be inflated to radially expand the prosthetic valve. In one embodiment, upon full expansion of the prosthetic valve 10, the skirt 18 can be forced into contact with the surrounding tissue of the native valve, establishing a seal between the outer surface of the frame 12 and the surrounding tissue.

When constructed of a self-expanding material, the prosthetic valve can be crimped to a radially compressed state and restrained in the compressed state by insertion into a sheath or equivalent mechanism of a delivery catheter. After the delivery apparatus is inserted into the body and advanced to position the prosthetic valve at the desired deployment location, the prosthetic valve can be advanced from the delivery sheath. As the prosthetic valve is deployed from the delivery sheath, the prosthetic valve can radially self-expand to its functional size.

It should be noted that the other embodiments of prosthetic valves disclosed herein can also be made from any of the plastically-expandable or self-expanding materials described above and can be implanted in the heart utilizing any of the delivery apparatuses and/or delivery techniques described above in connection with prosthetic valve 10.

In alternative embodiments, the prosthetic valve can be a surgically implanted prosthetic valve comprising a non-radially compressible and expandable frame on which the leaflets 20 are mounted in the arrangement shown in the drawings.

General Considerations

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present or problems be solved.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods. As used herein, the terms "a", "an", and "at least one" encompass one or more of the specified element. That is, if two of a particular element are present, one of these elements is also present and thus "an" element is present. The terms "a plurality of" and "plural" mean two or more of the specified element.

As used herein, the term "and/or" used between the last two of a list of elements means any one or more of the listed elements. For example, the phrase "A, B, and/or C" means "A", "B,", "C", "A and B", "A and C", "B and C", or "A, B, and C."

As used herein, the term "coupled" generally means physically coupled or linked and does not exclude the presence of intermediate elements between the coupled items absent specific contrary language.

In view of the many possible embodiments to which the disclosed principles may be applied, it should be recognized that the illustrated embodiments are only preferred examples and should not be taken as limiting the scope of the disclosure. Rather, the scope is defined by the following claims. We therefore claim all that comes within the scope and spirit of these claims.

We claim:

1. A prosthetic valve comprising:
   an annular frame having an inflow end, an outflow end, and a longitudinal axis extending from the inflow end to the outflow end; and
   a valve member mounted within the annular frame and located between the inflow end and the outflow end, comprising a plurality of at least three flexible leaflets, each leaflet comprising an inflow surface, an outflow surface, an inflow edge, and at least one articulating edge projecting in a direction away from the inflow edge and towards the outflow end,
   wherein adjacent leaflets are affixed to one another along their respective inflow edges,
   wherein the inflow edges are substantially non-articulating;
   wherein the articulating edges are articulable;
   wherein, when the prosthetic valve is deployed within a patient's body:
      the forward flow of blood through the prosthetic valve causes the leaflets to collapse radially inward to a collapsed state, defining an open configuration of the prosthetic valve, thereby creating a plurality of discrete flow areas between the frame and the inflow edges of the leaflets; and
      the reverse flow of blood through the prosthetic valve causes the leaflets to be pushed radially outward, defining a closed configuration of the prosthetic valve, thereby closing the plurality of discrete flow areas; and
   wherein each of the inflow edges extend between two points spaced circumferentially apart along an interior circumference of the frame, wherein the inflow edges of the adjacent leaflets are joined together directly without the aid of a mechanical support member extending between the points;
   wherein when the prosthetic valve is in the open configuration, a pocket is formed between the leaflets, wherein the pocket faces the outflow end and is bordered by the articulating edges and the outflow surfaces of the leaflets.

2. The prosthetic valve of claim 1, wherein the pocket is configured such that reverse flow entering into the pocket forces the leaflets radially outward.

3. The prosthetic valve of claim 1, wherein, in the open configuration, the inflow edges of the leaflets form a three-pointed star arrangement as seen viewed along the longitudinal axis from the inflow end to the outflow end.

4. The prosthetic valve of claim 1, wherein, in the closed configuration, the articulating edges are in contact with the frame and/or a skirt lining an interior surface of the frame.

5. The prosthetic valve of claim 1, wherein in the closed configuration, the outflow surfaces face the outflow end, and the inflow surfaces face the inflow end.

6. The prosthetic valve of claim 1, wherein the annular frame is a collapsible and expandable annular frame that is configured to be collapsed to a radially collapsed state for mounting on a delivery apparatus and expanded to a radially expanded state inside the body.

7. The prosthetic valve of claim 1, wherein the prosthetic valve is configured to be deployed within the patient's heart.

8. The prosthetic valve of claim 1, further comprising a skirt lining an interior surface of the annular frame.

9. The prosthetic valve of claim 1, wherein an outer surface of the prosthetic valve is configured to seal against surrounding tissue to prevent blood from flowing between the inflow end and the outflow end along the outer surface of the prosthetic valve when the prosthetic valve is deployed within the patient's body.

10. The prosthetic valve of claim 1, further comprising an outer skirt secured around an outside of the annular frame.

11. A prosthetic valve comprising:
    an annular frame having an inflow end, an outflow end, and a longitudinal axis extending from the inflow end to the outflow end; and
    a valve member mounted within the annular frame and located between the inflow end and the outflow end, comprising a plurality of at least three flexible leaflets, each leaflet comprising an inflow surface, an outflow surface, an inflow edge, and at least one articulating edge projecting in a direction away from the inflow edge and towards the outflow end,
    wherein adjacent leaflets are affixed to one another along their respective inflow edges,
    wherein the inflow edges are substantially non-articulating;
    wherein the articulating edges are articulable;
    wherein, when the prosthetic valve is deployed within a patient's body:
       the forward flow of blood through the prosthetic valve causes the leaflets to collapse radially inward to a collapsed state, defining an open configuration of the prosthetic valve, thereby creating a plurality of discrete flow areas between the frame and the inflow edges of the leaflets; and
       the reverse flow of blood through the prosthetic valve causes the leaflets to be pushed radially outward, defining a closed configuration of the prosthetic valve, thereby closing the plurality of discrete flow areas; and
    wherein each of the inflow edges extend between two points spaced circumferentially apart along an interior circumference of the frame, wherein the inflow edges of the adjacent leaflets are joined together directly without the aid of a mechanical support member extending between the points;
    further comprising a reinforcing fabric layer wrapped around joined portions of the inflow edges and sutures passing through the fabric layer and the inflow edges.

12. A prosthetic valve comprising:
    an annular frame having an inflow end, an outflow end, and a longitudinal axis extending from the inflow end to the outflow end; and
    a valve member mounted within the annular frame and located between the inflow end and the outflow end, comprising a plurality of at least three flexible leaflets;
    wherein each leaflet comprises a straight inflow edge, a convex scalloped articulating edge, wherein the articulating edge is convex and scalloped in the outflow direction, and two tabs disposed at opposite ends of the inflow edge, wherein adjacent tabs of adjacent leaflets are secured to each other to form commissures of the leaflets;
    wherein, when the prosthetic valve is deployed within a patient's body:
       the forward flow of blood through the prosthetic valve causes the leaflets to collapse radially inward to a collapsed state, defining an open configuration of the prosthetic valve, thereby creating a plurality of discrete flow areas between the frame and the inflow edges of the leaflets; and the reverse flow of blood through the prosthetic valve causes the leaflets to be pushed radially outward, defining a closed configuration of the prosthetic valve, thereby closing the plurality of discrete flow areas.

13. The prosthetic valve of claim 12, further wherein:
each of the inflow edges extend between two points spaced circumferentially apart along an interior circumference of the frame; and
wherein the inflow edges of adjacent leaflets are joined together directly without the aid of a mechanical support member extending between the points.

14. The prosthetic valve of claim 12, wherein the inflow edges lie in a plane perpendicular to the longitudinal axis.

15. The prosthetic valve of claim 12, wherein the inflow edge of each leaflet has portions affixed to portions of the inflow edges of two other leaflets.

16. The prosthetic valve of claim 12, further comprising sutures joining adjacent portions of the inflow edges of adjacent leaflets to each other.

17. The prosthetic valve of claim 12, further comprising a skirt lining an interior surface of the annular frame.

18. The prosthetic valve of claim 17, further comprising sutures joining the tabs to at least one of the annular frame and the skirt.

19. The prosthetic valve of claim 12, wherein when the prosthetic valve is in the open configuration, the inflow edges of the leaflets form a three-pointed star arrangement as seen viewed along the longitudinal axis from the inflow end to the outflow end.

* * * * *